United States Patent [19]

Hennekens

[11] Patent Number: 5,871,766

[45] Date of Patent: Feb. 16, 1999

[54] BETA-CAROTENE VITAMIN E THERAPY FOR INHIBITION OF MAJOR VASCULAR EVENTS

[75] Inventor: Charles H. Hennekens, Wellesley, Mass.

[73] Assignee: Brigham and Women's Hospital, Boston, Mass.

[21] Appl. No.: 361,159

[22] Filed: Dec. 21, 1994

Related U.S. Application Data

[63] Continuation of Ser. No. 956,459, Oct. 2, 1992, abandoned, which is a continuation of Ser. No. 592,024, Oct. 1, 1990, abandoned.

[51] Int. Cl.$^6$ .................. A61K 31/07; A61K 31/355; A61K 31/605

[52] U.S. Cl. .................. 424/422; 514/165; 514/824; 549/408

[58] Field of Search .................. 560/143; 424/422; 252/397; 514/165, 458, 558, 821, 822, 824; 549/408; 568/824

[56] References Cited

U.S. PATENT DOCUMENTS

| | | | |
|---|---|---|---|
| 3,853,993 | 12/1974 | Gainer | 514/25 |
| 4,304,784 | 12/1981 | Fujimura et al. | 514/443 |
| 4,491,574 | 1/1985 | Seifter et al. | 424/10 |
| 5,057,494 | 10/1991 | Sheffield | 514/12 |
| 5,153,001 | 10/1992 | Ismail | 424/455 |
| 5,221,668 | 6/1993 | Henningfield et al. | 514/23 |
| 5,278,189 | 1/1994 | Rath et al. | 514/561 |
| 5,310,554 | 5/1994 | Haigh | 424/439 |
| 5,326,757 | 7/1994 | Demopolous | 514/167 |
| 5,328,845 | 7/1994 | Finkelstein et al. | 435/254.1 |
| 5,346,488 | 9/1994 | Prince et al. | 606/7 |
| 5,422,247 | 6/1995 | Finklestein et al. | 435/67 |
| 5,589,468 | 12/1996 | Lin et al. | 514/52 |
| 5,607,839 | 3/1997 | Tsubokura et al. | 435/67 |
| 5,612,485 | 3/1997 | Schlipalius | 585/351 |
| 5,773,026 | 6/1998 | Schlipalius | 424/450 |

FOREIGN PATENT DOCUMENTS

| | | |
|---|---|---|
| 0 204 987 A1 | 12/1986 | European Pat. Off. . |
| 207 214 B | 11/1990 | Hungary . |
| 02-49091 | 2/1990 | Japan . |
| WO90/10440 | 9/1990 | WIPO . |

OTHER PUBLICATIONS

Morel et al., "Low Density Lipoprotein Cytotoxicity Induced by Free Radical Peroxidation of Lipid", *Journal of Lipid Research*, vol. 24, pp. 1070–1076 (1983).

Drug Facts and Comparisons; 44 Edition, Lippincott, pp. 6–7, 13–14, 60,62, 997–998.

Goodman, DeWitt S. Vitamin A and Retinoids in Health and Disease. The New England Journal of Medicine. 310(16), Apr. 19, 1984. pp. 1023–1031.

Council on Scientific Affairs, Chicago. Vitamin Preparations as Dietary Supplements and as Therapeutic Agents. JAMA, 257(14), Apr. 10, 1987. pp. 1929–1936.

Beta–Carotene, Vitamin A and E may not Prevent Cancer or Cardiovascular Diseases. WHO Drug Information. 11(1), (1997). pp 10–11.

Belanger, C. et al., "Preliminary Report: Findings from the Aspirin Component of the Ongoing Physician's Health Study," *New Engl. J. Med.* 318(4):262–264 (1988).

English Language Abstract of Hungarian Patent No. 207 214 B, Derwent World Patents Index, WPI Accession No. 93–177727 (1993).

English language translation of European Patent Application 0 204 987 A1.

Fedan, J.S., "Anticoagulant, Antiplatelet, and Fibrinolytic (Thrombolytic) Drugs," In: *Modern Pharmacology*, 3rd ed., Craig, C.R. and Stitzel, R.E., eds., Little Brown and Company: Boston (May 1990), pp. 370–385.

Afonsky, S.I., "Biochemistry of Animals," Moscow, pp. 235–236 (1970).

Mashkovsky, M.D., "Medicinal Substances," Part 2, Medicina Publishers, Moscow, pp. 37–38, 40–41, 190–191 (1988).

Partial English translations of documents AT9, AR10, AS10 and AT10.

Supplementary Partial European Search Report for European Patent Application No. 91919463.9 (Jul. 14, 1993).

Gey, K.F., On the Antioxidant Hypothesis with Regard to Arteriosclerosis, *Bibl. Nutr. Dieta* 37:53–91 (1986).

Nicol, M., Vitamines and antioxydantes et beta–carotène: activités préventives en pathologie humaine, *Med. et Nutr.* (France) 26:35–37 (1990).

Gaziano, J.M. et al., Dietary Antioxidants and Cardiovascular Disease, *Annals of the New York Academy of Sciences* 669:249–259 (1992).

Manson, J.E. et al., A Prospective Study of Antioxidant Vitamins and Incidence of Coronary Heart Disease in Women, *Circulation* 84(Supplement II):II–546, Abstract No. 2168 (1991).

Møgelvang, B., Can anti–oxidants be used to prevent ischemic vascular disorders?, *Nordisk Medicin* 107:53–56 (1992).

Morel, D.W. et al., Low density lipoprotein cytotoxicity induced by free radical peroxidation of lipid, *Journal of Lipid Research* 24:1070–1076 (1983).

van Hinsbergh, V.W.M. et al., Role of endothelial cells and their products in the modification of low–density lipoproteins, *Biochimica et Biophysica Acta* 878:49–64 (1986).

Leibovitz et al., Dietary Supplements of Vitamin E., β–Carotene, Coenzyme $Q_{10}$ and Selenium Protect Tissues Against Lipid Peroxidation in Rat Tissue Slices. *J. Nutr.* 120:97–104 (1990).

Parthasarathy et al., A role for endothelial cell lipoxygenase in the oxidative modification of low density lipoprotein, *Proc. Natl. Acad. Sci. USA* 86:1046–1050 (1989).

Steinberg et al., *New England J. Medicine* 320(14):915–924 (1989).

Smith et al., *Atherosclerosis* 75:105–109 (1989).

Carew et al., *PNAS USA* 84:7725–7729 (1987).

Gey et al., *Am. J. Clin. Nutr.* 45:1368–1377 (1987).

Kok et al., *Am. J. Clin. Nutr.* 45:462–468 (1987).

Hale et al., *J. Am. Diet. Assn.* 86(5):625–629 (1986).

Parthasarathy et al., *J. Clin. Invest.* 77:641–644 (1986).

Cathcart et al., *J. Leukocyte Biol.* 38:341–350 (1985).

Morel et al., *Arteriosclerosis* 4(4):357–364 (1984).

Burton et al., *Science* 224:569–573 (1984).

Kunio Yagi, *Bioessays* 1:58–60 (1984).

Hessler et al., *Arteriosclerosis* 3(3):215–222 (1983).

Fogelman et al., *PNAS USA* 77(4):2214–2218 (1980).

Gillilan et al., *Am. Heart J.* 93(4):444–449 (1977).

Knut Haeger, *Am. J. Clin. Nutr.* 27:1179–1181 (1974).

Anderson et al., *Am. J. Clin. Nutr.* 27:1174–1178 (1974).

*Primary Examiner*—Robert H. Harrison
*Attorney, Agent, or Firm*—Sterne, Kessler, Goldstein, & Fox, P.L.L.C.

[57] ABSTRACT

This invention is directed to a method for inhibiting the occurrence of a major vascular event in a subject whereby a subject is administered beta-carotene and/or vitamin E, either alone or in combination. Beta-carotene and/or vitamin E is administered such that the subject's risk of experiencing a major vascular event is thereby reduced. In another preferred embodiment, beta-carotene in combination with aspirin is particularly effective.

The invention further includes pharmaceutical compositions comprising beta-carotene in combination with vitamin E.

19 Claims, 1 Drawing Sheet

BETA-CAROTENE VITAMIN E THERAPY FOR INHIBITION OF MAJOR VASCULAR EVENTS

This application is a continuation of application Ser. No. 07/956,459, filed Oct. 2, 1992, now abandoned which is a continuation of application Ser. No. 07/592,024, filed Oct. 1, 1990, now abandoned.

U.S. GOVERNMENT LICENSE RIGHTS

The U.S. Government has a paid-up license in this invention and the right in limited circumstances to require the patent owner to license others on reasonable terms as provided for by the terms of Grant Nos. HL-26490, HL-34595, CA-34944 and CA-40360 awarded by the National Institute of Health.

BACKGROUND OF THE INVENTION

1. Field of the Invention

The invention generally relates to the field of medicinal chemistry. More specifically, the invention relates to the administration of beta-carotene and/or vitamin E to inhibit the occurrence of a major vascular event. The invention is further directed to pharmaceutical compositions comprising beta-carotene in combination with vitamin E. In one embodiment, beta-carotene is administered in combination with aspirin.

2. Brief Description of the Background Art

Despite a recent decline in cardiovascular disease-related mortality, cardiovascular disease remains the leading cause of morbidity and mortality in men and women in the United States, accounting for 47% of all deaths in 1986 (Dept. of Health and Human Services, *Mortality Part B* 88–1114:170–95 (1988).

Recent evidence suggests that antioxidant therapy may prevent or impede atherogenesis. Free radical oxidation has been postulated to play a role in the pathogenesis of atherosclerotic disease (Steinberg et al., *N. Engl. J. Med.* 320(14):915–24 (1989)). Serum lipoproteins can become oxidized in vivo (Warso et al., *J. Clin. Invest.* 75:667–71 (1985)) and these may be more atherogenic than their unoxidized counterparts. Oxidized low density lipoprotein (LDL) can potentially promote atherogenesis by several mechanisms. First, these modified lipoproteins may be toxic to or alter function of arterial endothelium. Oxidized LDL is cytotoxic to cultured endothelial cells as well as fibroblasts in vitro (Hessler et al., *Arteriosclerosis* 3(3):215–22 (1983); Yagi, K., *Bioessays* 1:58–60 (1984)). This altered endothelium may permit diffusion of serum lipids into the subendothelium and/or alter the ability of the endothelium to prevent thrombosis. Second, oxidized LDL chemotactically attracts and immobilizes monocyte/macrophages (Quinn et al., *Proc. Natl. Acad. Sci.* 82:5949–53 (1985)), some of which are destined to become lipid-laden foam cells within atheromatous plaque (Schaffner et al., *Am. J. Pathol.* 100:57–73 (1980); Gerrity, R. G.,*Am. J. Pathol.* 103:181–90 (1981)). Finally, oxidized LDL is taken up into foam cells via a scavenger receptor more readily than unoxidized LDL (Fogelman et al., *Proc. Natl. Acad. Sci.* 77:2214–18 (1980); Goldstein et al., Proc. Natl. Acad. Sci. 76:333–37 (1979)). Thus oxidation of LDL may play an important role in the initiation and propagation of atherosclerosis.

Recent attention has focused on agents that may prevent the oxidation of LDL and thus impede or retard the progression of atherosclerosis. When incubated in various cell preparations, LDL will become oxidized (Morel et al., *Artheriosclerosis* 4:357–64 (1984); Cathcort et al., *J. Leukocyte Biol.* 38:341–50 (1985)). This process can be inhibited by the addition to the cell preparation of antioxidants such as butylated hydroxytoluene or vitamin E (Morel et al., *Artheriosclerosis* 4:357–64 (1984); Steinbrecher, et al., Arteriosclertosis 1:135–43 (1987)). LDL taken from patients treated with probucol, a cholesterol-lowering agent with lipid antioxidant properties, does not become oxidized in an endothelial preparation that does oxidize LDL from untreated patients (Parthasarathy et al., *J. Clin. Invest.* 77:641–44 (1986)). This in vitro data suggests that antioxidant therapy may reduce the rate of in vivo lipid oxidation. In addition, after controlling for its lipid-lowering effect, probucol reduced the rate of fatty-streak formation in Watanabe heritable hyperlipidemic rabbits (Carew et al., *Proc. Natl. Acad. Sci.* 84:7725–29 (1987)).

Beta-Carotene

Beta-carotene is naturally occurring provitamin A with lipid antioxidant properties. In addition, beta-carotene is lipid soluble and is concentrated in circulating lipids and atherosclerotic plaques. Patients treated with a six week course of 160 mg of beta-carotene daily had a 50 fold increase in beta-carotene level within carotid plaques excised at the time of endarterectomy (Prince et al., *Circulation* 78:338–44 (1988)).

In vitro, beta-carotene is an unusual type of chain breaking lipid antioxidant (Burton et al., *Science* 224:569–73 (1984)). Because of its many conjugated double bonds, beta-carotene exhibits good radical trapping antioxidant behavior only at oxygen tension below 150 torr. Physiologic oxygen tension are typically below 100 torr.

There are few dietary studies on the association of beta-carotene to atherosclerotic disease. A cross-cultural study failed to show any association between serum beta-carotene levels and ischemic heart disease (Kok et al., *Am. J. Clin. Nut.* 45:462–68 (1987)).

Beta-carotene has virtually no important side effects. No biochemical or hematologic abnormalities were noted in 133 patients with erythropoietic protoporphyria treated with an average of 180 mg per day (doses as high as 300 mg per day) for as long as five years. The only reported side effect was skin discoloration, which is not evident at lower doses. In addition, one patient reported loose stools, which cleared spontaneously (Mathews-Roth et al., *Arch. Dermatol.* 113:1299–1232 (1977)).

Vitamin E

Vitamin E (alpha-tocopherol) is a fat soluble vitamin found in vegetable oils, egg yolk, milk fat, nuts, and cereal grains. Its primary functions is felt to be as a lipid antioxidant protecting lipids from oxidative modification.

In vitro data confirm the ability of vitamin E to prevent the oxidation of lipids. During incubation with cultured endothelial cells, the LDL particle undergoes various structural changes that will alter its metabolism. These changes are dependent on lipid peroxidation as an initial step. This oxidative modification can be totally inhibited by the addition of vitamin E to the cellular preparation (Morel et al., *Atherosclerosis* 4:357–64 (1984)).

Cross-cultural studies suggest an association between lipid standardized vitamin E levels and ischemic heart disease. In a large cross-cultural survey in which serum was collected from 903 randomly selected males aged 40–49 to determine the relationship of cholesterol-standardized vitamin E levels to rates of ischemic heart disease in six study populations (Gey et al., Am. J. Clin. Nutr. 45: 1368–77 (1987)), the vitamin E level within the plasma lipoproteins as indicated by the vitamin E/cholesterol ration revealed significant inverse correlation to the ischemic heart disease mortality rate in each study population. In a nested case-control study of Dutch men, no significant associations between serum vitamin E levels and cardiovascular disease mortality were noted (Kok, et al., Am. J. Clin. Nut. 45:462–68 (1987)). However, vitamin E levels were not lipid standardized. In animal studies, restricted ovulatory hens, which develop hyperlipidemia and subsequent aortic intimal thickening, were fed 1000 mg of vitamin E per Kg of feed (Smith et al., Atherosclerosis 75:105–09 (1989)). Compared to controls, those fed a vitamin E diet had reduced levels of plasma peroxides and less aortic intimal thickening.

Variable results have been obtained from randomized clinical trials using vitamin E in various forms of atherosclerotic vascular disease. After 40 months of treatment with 600 mg of vitamin E daily in patients with claudication, 13 of 17 in the treatment group compared to only 2 of 17 in the placebo group showed improvement in symptoms (Livingston et al., Lancet. 2:602–04 (1958)). These results have been confirmed in subsequent randomized trials (Haeger et al., Am. J. Clin. Nutr. 27:1179–81 (1974)). A randomized, placebo-controlled, double-blind, cross-over study among patients with angina pectoris failed to show a benefit after six months of therapy with 1600 mg of vitamin E daily (Gillilan et al., Am. Heart J. 93:444–49 (1977)).

Vitamin E is a safe drug with few clinically important side effects. Animal studies have shown that vitamin E is not carcinogenic or teratogenic (Federation of American Societies for Experimental Biology, Washington DC, (1975)). In human studies few side effects have been reported in double-blind protocols and other large studies, even at high doses (Anderson et al., Am. J. Clin. Nutr. 27:1174–78 (1974); Hole et al., J. Am. Diet. Assoc. 86:625–29 (1986)). Although oral intake of vitamin E at doses of 1200 mg/day may increase bleeding time in cardiac patients on warfarin (Corrigan et al., J.A.M.A. 230:1300–01 (1974), vitamin E has not been shown to produce any coagulation abnormalities at lower doses among patients on warfarin or at any dose among individuals who are not vitamin K-deficient.

SUMMARY OF THE INVENTION

We have discovered that the administration of Beta carotene and/or Vitamin E, either alone or in combination, to a subject, inhibits the occurrence of one or more major vascular events in the subject. Major vascular events include, myocardial infarction, stroke, coronary revascularization procedure and cardiovascular death.

In particular, we have discovered that the occurrence of one or more major vascular events in a human subject that has experienced or is predisposed to experience angina pectoris, coronary artery bypass graft and/or percutaneous transluminal coronary angioplasty, is inhibited by the administration of beta-carotene and/or vitamin E to the subject.

This invention is further directed to a pharmaceutical composition comprising the synergistic combination of beta-carotene and vitamin E. The combination of beta-carotene and vitamin E is particularly useful in the therapeutic methods of the invention.

In yet a further embodiment, beta-carotene is administered in combination with aspirin.

FIGURES

FIG. 1 is a graphic representation of relative risk adjusted for age and aspirin assignment of major vascular events in the beta-carotene group, as compared with the placebo group, according to year of follow-up in the trial. Vertical bars represent confidence intervals. The number of events for each interval are listed below each bar.

FIG. 1 also shows that the effect of beta-carotene is chronic, not acute, and that beta-carotene delays the progression of atherosclerosis.

DESCRIPTION OF THE PREFERRED EMBODIMENTS

Figure 1:
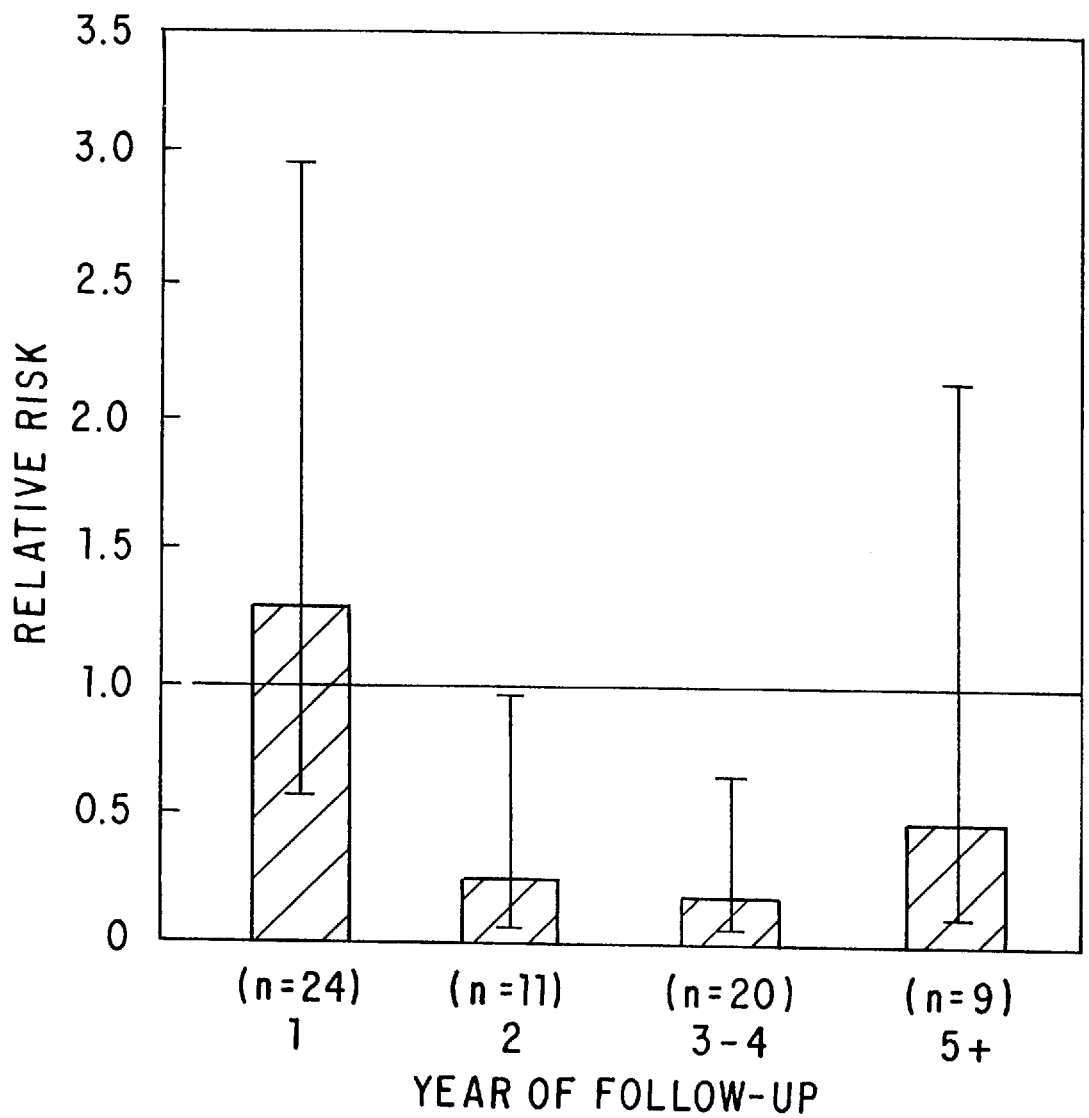

A preferred method of the invention includes the administration of beta-carotene and/or vitamin E to a subject such that the occurrence of one or more major vascular events is thereby inhibited.

Another preferred method of the invention includes the administration of a composition comprised of the synergistic combination of beta-carotene and vitamin E to a subject such that the occurrence of one or more major vascular events is thereby reduced. Included as well in the present invention are pharmaceutical compositions comprised of beta-carotene and vitamin E in combination with a pharmaceutically acceptable carrier.

More specifically, by the term "inhibiting" is intended both prevention and amelioration of the disease state. Thus the invention comprises both a therapeutic and a prophylactic modality.

By the term "major vascular events" is generally intended atherosclerotic vascular disease and its related illnesses. In particular, major vascular events includes myocardial infarction, stroke, coronary revascularization procedure and cardiovascular death.

By the term "beta-carotene" is intended beta-carotene and the biologically active analogs thereof. Typical analogs include molecules which demonstrate equivalent biological function but which differ structurally. Such analogs include canthaxanthin, astaxanthin, zeaxanthin, lutein and lycopene.

By the term "vitamin E" is intended vitamin E and the biologically active analogs thereof. Typical analogs include molecules which demonstrate equivalent biological function but which differ structurally. Such analogs include all other tocopherols.

By the term "aspirin" is intended aspirin and the biologically active fractions thereof.

By the term "a composition of beta-carotene in combination with vitamin E" is intended any composition comprising beta-carotene or beta-carotene analogs, and vitamin E or analogs of vitamin E.

By the term "a composition of beta-carotene in combination with aspirin" is intended any composition comprising beta-carotene or beta-carotene analogs, and aspirin or analogs of aspirin.

By the term "subject" is intended all mammals, in particular humans.

By the term "administration" is intended the administration of the pharmaceutical compositions of the present invention by any means that achieve their intended purpose. For example, administration may be by parenteral, subcutaneous, intravenous, intramuscular, intra-peritoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

Compositions within the scope of this invention include all compositions of 500 mg or less of beta-carotene, in combination with 5000 mg or less of vitmamin E; and all compositions of 500 mg or less of beta-carotene, in combination with 2400 mg or less of aspirin, in an amount which is effective to achieve its intended purpose. While individual needs vary, determination of optimal ranges of effective amounts of each component is with the skill of the art. Typically, beta-carotene and/or vitamin E may be administered to mammals, e.g. humans, orally at a dose of 25–300 mg per day of beta carotene and 100–3200 mg per day of vitmin E, or an equivalent amount of beta-carotene, vitamin E and the beta-carotene/vitamin E composition, per day of the body weight of the mammal being treated for major vascular disorders. Preferably, about 50 mg of beta-carotene and/or 600 mg of vitamin E are orally administered to treat or prevent such disorders.

The unit oral dose may comprise from about 0.25 to about 500 mg, preferably about 3 to about 100 mg of beta-carotene; about 5 to about 5000 mg, preferably about 100 to about 1000 mg of vitamin E; and about the same relative amounts of each for the composition combining beta-carotene and vitamin E. The unit dose may be administered one or more times daily or on alternate days.

In addition to administering beta-carotene and/or vitamin E as a raw chemical, the compounds may be administered as part of a pharmaceutical preparation containing suitable pharmaceutically acceptable carriers, excipients and auxiliaries which facilitate processing of beta-carotene and/or vitamin E into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, in dose ranges that provide similar bioavailability as described above, together with the excipient.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, steric acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers-may be added.

Possible pharmaceutical preparations which can be used rectally include, for example, suppositories, which consist of a combination of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers.

The entire text of all applications, patents and publications, if any, cited above and below are hereby incorporated by reference.

EXAMPLES

Having now described the invention, the same will be more readily understood through reference to the following examples which are provided by way of illustration, and are not intended to be limiting of the present invention.

Example 1

A study was conducted in which a randomized trial of aspirin was tested for its effect on the reduction of cardiovascular mortality; and beta-carotene (provided as LUROTIN™ by BASF) was simultaneously tested for its effect on the reduction of cancer incidence. The trial was conducted entirely by mail among 22,071 male physicians, aged 40 to 84, who were randomized to take either a 325 mg aspirin or placebo tablet every other day alternating with a capsule containing 50 mg beta-carotene or placebo. The trial thus used a 2×2 factorial design, with each participant taking one pill daily (Stampfer et al., *Stat. Med* 4:111–16 (1985)).

The 261,248 potentially eligible physicians, identified from an age-targeted list provided by the American Medical Association, were sent letters of introduction, consent forms and enrollment questionnaires. A total of 33,223 doctors enrolled in an 18-week run-in phase. Participants took daily pills from calendar packs containing active aspirin alternating with beta-carotene placebo. This run-in period enabled the identification and elimination of poor compilers and those who could not tolerate aspirin before randomization, thus increasing the power of the study. At the end of the run-in, a total of 22,071 (66%) were randomized to aspirin, beta-carotene, both or neither. Use of the run-in strategy appears to have been quite effective. At 60.2 months of follow-up, (averaged for participants, ranging from 45.8 to 77.0) over 90% of all participants reported taking 50% or more of their study pills for the entire duration of the trial, 86.7% were still taking the beta-carotene/placebo capsules, and 84% were still taking the aspirin/placebo tablets. Not a single participant has been lost with respect to mortality follow-up, and 99.7% are still providing information on morbidity. The blinded aspirin component of the study was terminated prematurely due primarily to the emergence of a statistically extreme benefit of aspirin on both fatal and nonfatal MI (The Steering Committee of the Physicians' Health Study Research Group, *N. Engl. J. Med.* 318:262–64 (1988)), while the beta-carotene component is still ongoing.

Of particular relevance to the present invention are the studies concerning beta-carotene's role in cardiovascular disease. These studies were conducted among the subgroup of participants who entered the trial with a history of angina pectoris or coronary revascularization (coronary artery bypass surgery or percutaneous transluminal angioplasty), and indicated a marked and statistically significant benefit of beta-carotene in reducing subsequent vascular events among this high-risk population.

The results, as set forth in Table 1, indicate that the reduction of risk for patients taking beta-carotene, as compared to placebo, did not occur until beta-carotene had been taken for a long period of time.

TABLE 1

Cardiovascular End Points in Patients With Prerandomization Angina Pectoris and/or Coronary Revascularization According to Beta Carotene Assignment*.

| | Beta Carotene (n = 160) | Placebo (n = 173) | Relative Risk** | 95% Confidence Interval | P Value |
|---|---|---|---|---|---|
| Revascularization (Revasc.)*** | 10 | 21 | 0.43 | 0.17–1.11 | 0.08 |
| Myocardial Infarction (MI) | 10 | 17 | 0.61 | 0.31–1.40 | 0.29 |
| Stroke | 4 | 9 | 0.47 | 0.15–1.55 | 0.22 |
| Cardiovascular Death (CV Death) | 7 | 6 | 1.29 | 0.42–4.01 | 0.66 |
| Total Death | 8 | 10 | 0.85 | 0.29–2.51 | 0.77 |
| Major coronary event (Revasc., MI, Coronary Death) | 20 | 36 | 0.56 | 0.31–0.99 | 0.047 |
| Major vascular event (Major coronary event, Stroke) | 22 | 42 | 0.51 | 0.30–0.88 | 0.015 |

*End Points included only the first event within each category.
**Adjusted for age and aspirin assignment.
***Defined as coronary artery bypass graft or percutaneous transluminal angioplasty.

What is claimed is:

1. A method for ameliorating a major vascular event selected from the group consisting of myocardial infarction, stroke, coronary revascularization and cardiovascular death in a mammalian subject, said method consisting of administering the lipid soluble carotenoid beta-carotene to said mammalian subject in an amount which is effective to ameliorate said major vascular event.

2. The method of claim 1, wherein said beta-carotene is administered to said mammalian subject subcutaneously.

3. The method of claim 1, wherein said beta-carotene is administered to said mammalian subject orally.

4. The method of claim 1, wherein said beta-carotene is administered to said mammalian subject in an amount ranging from 0.25 mg to 500 mg on alternate days or daily.

5. The method of claim 1, wherein said mammalian subject is a human subject that has angina pectoris and/or coronary revascularization.

6. The method of claim 5, wherein said coronary revascularization is selected from the group consisting of coronary artery bypass graft or percutaneous transluminal coronary angioplasty.

7. A method for ameliorating a major vascular event selected from the group consisting of myocardial infarction, stroke, coronary revascularization and cardiovascular death in a mammalian subject, said method comprising administering a composition consisting of the lipid soluble carotenoid beta-carotene in combination with vitamin E to said mammalian subject in an amount which is effective to ameliorate said major vascular event.

8. The method of claim 7, wherein said composition is administered to said mammalian subject subcutaneously.

9. The method of claim 7, wherein said composition is administered to said mammalian subject orally.

10. The method of claim 7, wherein said composition is administered to said mammalian subject in an amount ranging from 0.25 mg to 500 mg of said beta-carotene, and 5 mg to 5000 mg of said vitamin E on alternate days or daily.

11. The method of claim 7, wherein said mammalian subject is a human subject that has angina pectoris and/or coronary revascularization.

12. The method of claim 11, wherein said coronary revascularization may be either one or more coronary artery bypass graft(s), or one or more percutaneous transluminal coronary angioplasty(s).

13. A method for ameliorating a major vascular event selected from the group consisting of myocardial infarction, stroke, coronary revascularization and cardiovascular death in a mammalian subject, said method comprising administering a composition consisting of the lipid soluble carotenoid beta-carotene in combination with aspirin to said mammalian subject in an amount which is effective to ameliorate said major vascular event.

14. The method of claim 13, wherein said composition is administered to said mammalian subject subcutaneously.

15. The method of claim 13, wherein said composition is administered to said mammalian subject orally.

16. The method of claim 13, wherein said composition is administered to said mammalian subject in an amount ranging from 0.25 mg to 500 mg of said beta-carotene, and 5 mg to 2400 mg of said aspirin on alternate days or daily.

17. The method of claim 13, wherein said mammalian subject is a human subject that has angina pectoris and/or coronary revascularization.

18. The method of claim 17, wherein said coronary revascularization may be either one or more coronary artery bypass graft(s), or one or more percutaneous transluminal coronary angioplasty(s).

19. A pharmaceutical composition suitable for ameliorating a major vascular event selected from the group consisting of myocardial infarction, stroke, coronary revascularization and cardiovascular death in a subject, said composition comprising aspirin and an analog of beta-carotene selected from the group consisting of canthaxanthin, astaxanthin, zeaxanthin, lutein and lycopene.

* * * * *